US011318456B2

(12) United States Patent
Makino et al.

(10) Patent No.: US 11,318,456 B2
(45) Date of Patent: May 3, 2022

(54) ASEPTIC SAMPLING APPARATUS AND SAMPLING METHOD USING THE SAME

(71) Applicants: NIHON KOHDEN CORPORATION, Tokyo (JP); OSAKA UNIVERSITY, Osaka (JP)

(72) Inventors: Hodaka Makino, Tokorozawa (JP); Hirotsugu Kubo, Tokorozawa (JP); Tetsuya Ogawa, Tokorozawa (JP); Masahiro Kinooka, Suita (JP)

(73) Assignees: NIHON KOHDEN CORPORATION, Tokyo (JP); OSAKA UNIVERSITY, Osaka (JP)

( * ) Notice: Subject to any disclaimer, the term of this patent is extended or adjusted under 35 U.S.C. 154(b) by 255 days.

(21) Appl. No.: 16/239,088

(22) Filed: Jan. 3, 2019

(65) Prior Publication Data
US 2019/0247842 A1    Aug. 15, 2019

(30) Foreign Application Priority Data

Feb. 14, 2018   (JP) ............................ JP2018-024419

(51) Int. Cl.
*B01L 3/00*        (2006.01)
*B01L 1/00*        (2006.01)
(Continued)

(52) U.S. Cl.
CPC ............... *B01L 1/025* (2013.01); *B01L 3/502* (2013.01); *B01L 3/565* (2013.01); *B01L 3/567* (2013.01);
(Continued)

(58) Field of Classification Search
CPC ....... B01L 1/025; B01L 3/502; B01L 2300/10
See application file for complete search history.

(56) References Cited

U.S. PATENT DOCUMENTS 5,690,895 A * 11/1997 Matsumoto ........ G01N 15/1404
356/246
2006/0234372 A1* 10/2006 Donahue ................ C12M 35/04
435/293.1
(Continued)

FOREIGN PATENT DOCUMENTS

JP       56-135160 A      10/1981
JP       6-281557 A       10/1994
(Continued)

OTHER PUBLICATIONS

Communication dated Sep. 28, 2021 issued by the Japanese Intellectual Property Office in English counterpart Japanese Application No. 2018-024419.

*Primary Examiner* — Nathan A Bowers
(74) *Attorney, Agent, or Firm* — Sughrue Mion, PLLC

(57) ABSTRACT

An aseptic sampling apparatus includes an isolator, a liquid delivery port that is disposed in the isolator, a sampling section that is disposed inside the isolator, a first flow path that communicates with a discharge flow path of the sampling section, and that connects an inside and outside of the isolator to each other through the liquid delivery port, a fluid supplying unit that supplies a fluid to the sampling section, a gas supplying unit that communicates with the fluid supplying unit, and a seal member that prevents the fluid supplied from fluid supplying unit to the discharge flow path from leaking.

11 Claims, 10 Drawing Sheets

(51) Int. Cl.
*B01L 1/02* (2006.01)
*C12M 1/34* (2006.01)

(52) U.S. Cl.
CPC .............. *C12M 41/00* (2013.01); *B01L 3/563* (2013.01); *B01L 2200/0673* (2013.01); *B01L 2200/141* (2013.01); *B01L 2300/048* (2013.01); *B01L 2300/049* (2013.01); *B01L 2300/10* (2013.01); *B01L 2400/06* (2013.01); *B01L 2400/0622* (2013.01); *B01L 2400/0644* (2013.01)

(56) References Cited

U.S. PATENT DOCUMENTS

| | | | |
|---|---|---|---|
| 2008/0213872 A1* | 9/2008 | Regan | G16H 10/40 |
| | | | 435/283.1 |
| 2012/0252110 A1 | 10/2012 | Oura et al. | |
| 2013/0109086 A1* | 5/2013 | Kobayashi | C12M 23/44 |
| | | | 435/297.1 |
| 2016/0332157 A1* | 11/2016 | Uda | G01N 1/00 |
| 2017/0008755 A1* | 1/2017 | Ishida | B05B 1/086 |
| 2020/0009549 A1* | 1/2020 | Ham | B01L 3/502 |

FOREIGN PATENT DOCUMENTS

| | | |
|---|---|---|
| JP | 7-159415 A | 6/1995 |
| JP | 2004-93194 A | 3/2004 |
| JP | 2012-200239 A | 10/2012 |
| WO | 2012/002497 A1 | 1/2012 |

* cited by examiner

ASEPTIC SAMPLING APPARATUS AND SAMPLING METHOD USING THE SAME

CROSS REFERENCE TO RELATED APPLICATION

This application is based on Japanese Patent Application No. 2018-024419 filed on Feb. 14, 2018, the contents of which are incorporated herein by reference.

BACKGROUND

The presently disclosed subject matter relates to an aseptic sampling apparatus, and to a sampling method using the aseptic sampling apparatus.

In technical fields in which cells must be cultured, such as regenerative medicine, an apparatus that cultures cells for a long term while maintaining a sterile environment has been developed. In order to check the conditions of cells which are cultured in such an apparatus, a culture solution and the like must be taken out to a non-sterile environment while maintaining sterile environment. In the case where a culture solution in a cell incubator is to be subjected to a sampling operation, conventionally, a sample in an incubator that is sterile space must be once carried into a pass box or the like that is disposed adjacent to the incubator to take the sample to the outside, and therefore the sampling operation is time-consuming.

As a countermeasure against the matter, a sampling system of the isolator type in which a plurality of cell incubators can be accommodated in an incubator that is maintained in a sterile environment has been proposed (for example, JP-A-2012-200239).

In the system, in order to maintain a sterile environment, a one-way valve is provided to limit a flow of liquid to a unidirectional flow from the inside to the outside of an isolator, thereby maintaining sterility inside an isolator.

The conventional sampling system is configured so that a sample is delivered from the sterile environment to a non-sterile environment by using a pressure which is generated by a tube pump. In order to move the sample to a predetermined place, therefore, a sample amount depending on the length of a tube is required. Moreover, the sample must be mixed with a buffer solution or the like in order to ensure a sample amount which enables the transportation using the tube pump to be realized. The presently disclosed subject matter provides an aseptic sampling apparatus in which, even in the case where the amount of a sample is small, sampling is enabled while maintaining a sterile environment of the interior of an isolator. The presently disclosed subject matter further provides a sampling method using the aseptic sampling apparatus.

The inventors have intensively studied the matter, and developed an aseptic sampling apparatus in which, in a flow path connecting the inside and outside of an isolator to each other, a sample is interposed between a first gas and a second gas, and the second gas is sent into the flow path, whereby, even in the case where the amount of the sample is small, the sample is enabled to be delivered from a sterile environment in the isolator to a non-sterile environment, and also a sampling method using the apparatus. That is, the presently disclosed subject matter includes the following configurations.

SUMMARY OF THE INVENTION

[1] According to an aspect of the presently disclosed subject matter, an aseptic sampling apparatus includes:

an isolator;
a liquid delivery port which is disposed in the isolator;
a sampling section which is disposed inside the isolator;
a first flow path which communicates with a discharge flow path of the sampling section, and which connects an inside and outside of the isolator to each other through the liquid delivery port;
a fluid supplying unit which supplies a fluid to the sampling section:
a gas supplying unit which communicates with the fluid supplying unit; and
a seal member which prevents the fluid supplied from fluid supplying unit to the discharge flow path from leaking.

[2] The aseptic sampling apparatus according to [1], wherein the seal member is disposed in a part of the discharge flow path.

[3] The aseptic sampling apparatus according to [1] or [2], wherein the apparatus further includes at least one one-way valve which is disposed in the first flow path, and which limits flow of the fluid in the first flow path to a direction from the sampling section toward the liquid delivery port.

[4] The aseptic sampling apparatus according to any one of [1] to [3], wherein the apparatus further includes a sample recovering unit which communicates with the first flow path in downstream of the liquid delivery port.

[5] The aseptic sampling apparatus according to [4], wherein the sample recovering unit is a valve unit.

[6] The aseptic sampling apparatus according to any one of [1] to [5], wherein the apparatus further includes:
a second flow path which communicates with the sampling section;
a buffer solution supplying section which supplies the fluid to the second flow path; and
a first pump which is disposed in the second flow path.

[7] The aseptic sampling apparatus according to any one of [1] to [6], wherein the apparatus further includes:
third and fourth flow paths which branch from the first flow path in downstream of the liquid delivery port;
a valve switching unit which switches a flow path to one of the third and fourth flow paths; and
a second pump which is disposed in the third flow path or the fourth flow path.

[8] The aseptic sampling apparatus according to any one of [1] to [6], wherein an aseptic connection coupling is disposed in the first flow path and in downstream of the liquid delivery port.

[9] The aseptic sampling apparatus according to any one of [1] to [8], wherein the gas supplying unit is a syringe.

[10] The aseptic sampling apparatus according to any one of [1] to [9], wherein the seal member is an O-ring.

[11] A sampling method wherein, in the aseptic sampling apparatus according to any one of [1] to [10], the method includes the steps of:

(1) in the first flow path in which a first gas exists, supplying a sample after the first gas, by the fluid supplying unit; and (2) after the sample in the first flow path, supplying a second gas by the fluid supplying unit, to deliver the sample to an outside of the isolator.

According to the presently disclosed subject matter, even in the case where the amount of a sample is small (for example, 1 mL or smaller), the sample can be recovered while maintaining a sterile environment in the isolator, and suppressing mixture of the sample with a buffer solution or the like to a minimum level.

DETAILED DESCRIPTION OF EMBODIMENTS

Figure 1A:
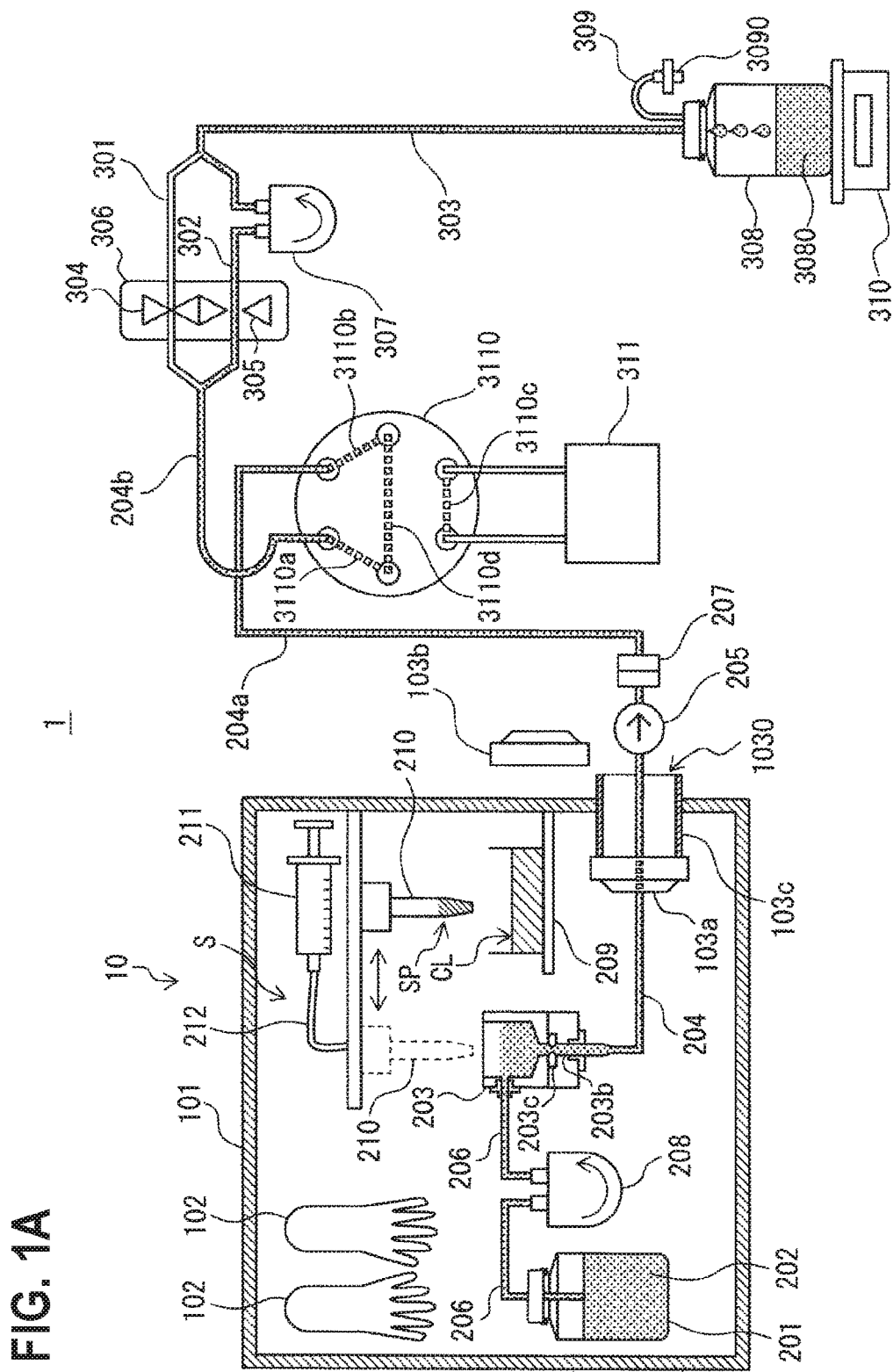
FIGS. 1A to 1D are schematic diagrams of an aseptic sampling apparatus of an embodiment of the presently disclosed subject matter.

Hereinafter, the presently disclosed subject matter will be described by way of embodiments thereof. However, the following embodiments are not intended to limit the presently disclosed subject matter as defined in the appended claims, and all combinations of features described in the embodiments are not always essential to solving means of the presently disclosed subject matter.

<Aseptic Sampling Apparatus>

FIGS. 1A to 1D illustrates schematic diagrams of an aseptic sampling apparatus 1 of an embodiment of the presently disclosed subject matter. In the embodiment, the aseptic sampling apparatus 1 may include:

an isolator 10 which maintains the internal space in an aseptic condition;

a liquid delivery port 103 which is disposed in the isolator 10;

a sampling section 203 which is disposed inside the isolator 10;

a first flow path 204 which communicates with a discharge flow path 203b of the sampling section 203, and which connects the inside and outside of the isolator 10 to each other through the liquid delivery port 103;

a fluid supplying unit 210 which supplies a fluid to the sampling section 203;

a gas supplying unit 211 which communicates with the fluid supplying unit 210; and a seal member 203c which prevents the fluid supplied from fluid supplying unit 210 to the discharge flow path 203b from leaking.

The isolator 10 is an apparatus which has an aseptic operation area that is completely physically isolated from direct interventions of the environment and an operator. Air filtered by a HEPA filter or an ULPA filter is supplied into the isolator after decontamination to be continuously used while preventing risk of contamination from the external environment. The isolator 10 in FIG. 1 is isolated from the external space by an aseptic chamber 101, and, although not illustrated, may include a HEPA filter or an ULPA filter. Although not illustrated, the isolator 10 may further include a decontaminating unit which decontaminates the internal space S of the isolator. The term "decontamination" means a process of eliminating living microorganisms by a reproducible method, or that of reducing living microorganisms to a pre-designated level. The decontaminating unit is a unit which is used for realizing "decontamination." For example, a unit using a decontamination agent, that performing a plasma process, that using gamma rays, or that using ultraviolet rays may be employed as the decontaminating unit, but the decontaminating unit is not limited to such units. Preferably, a unit using a decontamination agent may be used. Examples of the decontamination agent are mist or vapor of hydrogen peroxide or peracetic acid, an ozone gas, a chlorine dioxide gas, and an ethylene oxide gas. When such a decontaminating unit is used, the internal space S of the isolator is decontaminated.

A liquid delivery port body 103c is disposed in the aseptic chamber 101 which isolates the inside and outside of the isolator 10 from each other. The liquid delivery port body 103c may have a cylindrical shape, or a hollow rectangular parallelepiped shape. The shape of the liquid delivery port body is not particularly limited. The inside and outside of the aseptic chamber 101 communicate with each other through the liquid delivery port body 103c. A liquid delivery port inner lid 103a and a liquid delivery port outer lid 103b can be fitted to liquid delivery port openings 1031, 1030 of the liquid delivery port body 103c, respectively to hermetically seal the liquid delivery port openings 1031, 1030. The liquid delivery port 103 may include at least the liquid delivery port inner lid 103a, the liquid delivery port outer lid 103b, and the liquid delivery port body 103c. The first flow path 204 is passed through the liquid delivery port inner lid 103a. The portion of the liquid delivery port inner lid 103a through which the first flow path 204 is passed is sealed by a sealing member or the like so that the fluid does not leak.

The first flow path 204 communicates with the discharge flow path 203b of the sampling section 203. The sample or buffer solution 202 which is supplied to the sampling section 203 passes through the first flow path 204 that communicates with the discharge flow path 203b of the sampling section 203, and then is discharged to the outside of the isolator 10. The seal member 203c which prevents the fluid supplied from the fluid supplying unit 210 from leaking is disposed in a part of the discharge flow path 203b of the sampling section 203. The seal member 203c enables the fluid such as a gas or a liquid such as the sample SP or buffer solution 202 which is supplied from the fluid supplying unit 210, to be sent into the first flow path 204 while being pressurized. The seal member 203c is requested to have a function in which, when a tip end portion of the fluid supplying unit 210 is inserted into a discharge port 203a, the seal fills a gap between the discharge flow path 203b and the fluid supplying unit 210 to prevent the fluid from leaking. For example, the seal member may be an O-ring, a packing, a hollow seal member which is expanded by injecting a gas or a liquid into the inside of the member, or the like. The O-ring may have a typical doughnut-like shape, or another shape such as a triangle, a rectangle, a polygon, or an ellipse. In the O-ring, any adequate shape may be employed as far as the O-ring can exert the function of preventing a liquid from leaking in the case where the O-ring is used in combination with the fluid supplying unit 210. Alternatively, a structure for preventing a liquid from leaking may be realized by forming male and female thread structures (the reverse may be possible) in parts of the fluid supplying unit 210 and the discharge flow path 203b. An O-ring is preferably used as the seal member 203c. As the material of the seal member 203c, a known material may be used, and preferably a material which is resistant to a sterilizing process. For example, the material may be a metal (for example, stainless steel), polyethylene, polypropylene, polycarbonate, polystyrene, polyvinyl chloride, nylon, polyurethane, polyurea, polylactate, polyglycolic acid, polyvinyl alcohol, polyvinyl acetate, poly(meta)acrylic acid, a poly (meta)acrylic acid derivative, polyacrylonitrile, poly(meta)acrylamide, a poly(meta)acrylamide derivative, polysulfone, polycarbonate, cellulose, a cellulose derivative, polysilicone, glass, and ceramics.

The aseptic sampling apparatus 1 of the embodiment of the presently disclosed subject matter may include the fluid supplying unit 210 for supplying the fluid to the sampling section 203. The fluid supplying unit 210 changes the internal air pressure to a negative pressure or a positive pressure, whereby the fluid can be sucked or discharged. For example, a pipette, a tube, or the like can be employed as the fluid supplying unit. In the case where the fluid supplying unit 210 is a pipette, preferably, a tip end portion of the pipette may be a replaceable disposal pipette tip. When a disposal pipette tip is used, the tip can be easily replaced with a new one for every samples, and cross contamination among samples can be prevented from occurring. As a disposal pipette tip, a commercially available one can be used. In accordance with the amount and use of a sample to be handled, for example, useful are pipette tips for capacities of 1 L, 10 µL, 20 µL, 100 µL, 200 µL, 250 µL, 300 µL, 500 µL, 1,000 µL, 1,200 µL, 2,000 µL, and more. In order to prevent cross contamination among samples from occurring, the fluid supplying unit 210 may have a filter.

In another embodiment, the tip end portion of the fluid supplying unit 210 may include a flange portion (not shown) which covers the discharge port 203a of the sampling section 203. In this case, the seal member 203c (for example, a packing or an O-ring) which prevents the fluid from leaking is disposed in the periphery of the flange portion or the discharge port 203a.

Figures 3A, 3B:
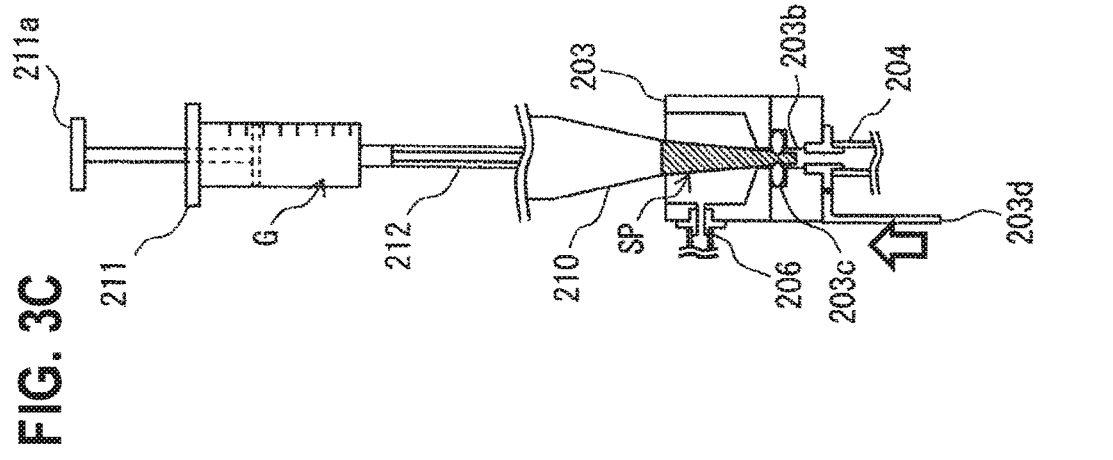
FIGS. 3A to 3F are schematic diagrams illustrating a part of the aseptic sampling apparatus of the embodiment of the presently disclosed subject matter.
Figure 3C:
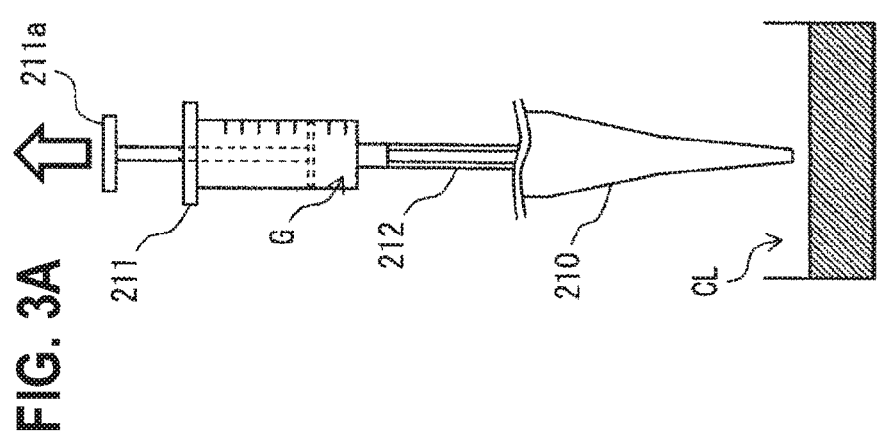
Figure 3D:
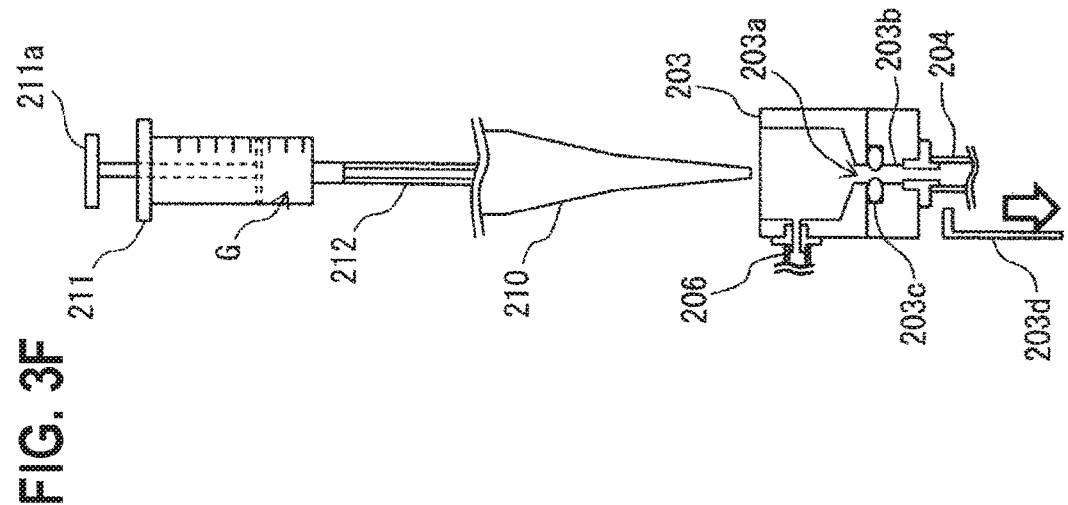

The aseptic sampling apparatus 1 may include the gas supplying unit 211 which communicates with the fluid supplying unit 210. The gas supplying unit 211 may include a mechanism which sends a gas G to the fluid supplying unit 210. The gas supplying unit 211 is requested to have a mechanism which sends the compressed gas G. For example, a syringe or a gas cylinder containing a compressed gas may be used as the gas supplying unit. Preferably, the gas supplying unit may include a function of sucking and discharging a gas. For example, a syringe may be employed. In the case where the gas supplying unit 211 is a syringe, when a piston 211a (see FIG. 3A) is pulled, the interior of the fluid supplying unit 210 is set to have a negative pressure, and the fluid can be sucked into the fluid supplying unit 210. When the piston 211a is pushed, the compressed gas G can be supplied into the fluid supplying unit 210. Preferably, the gas supplying unit 211 is a syringe because both suction and discharge of the fluid can be performed.

In the embodiment, the first flow path 204 of the aseptic sampling apparatus 1 may include at least one one-way valve 205 which limits flow of the fluid in the first flow path 204 to a direction from the sampling section 203 toward the liquid delivery port 103. This can prevent the fluid from reversely flowing into the internal space S of the isolator.

Preferably, the inner wall of the first flow path 204 has a low liquid wettability, i.e., has a hydrophobic property. Even in the case where the amount of the sample SP is small, this can prevent the sample SP from adhering to the inner wall of the first flow path 204, and therefore the sample SP can be efficiently delivered to the outside of the isolator 10. As the first flow path 204, a tube which can be sterilized, and which is flexible may be used, and for example a medical tube (e.g., a silicone rubber tube, a polyethylene tube, a polyimide tube, or a fluorine resin tube) may be employed.

In the embodiment, the first flow path 204 may include an aseptic connection coupling 207 in the middle of the flow path. In the aseptic connection coupling 207, an aseptic connection coupling (male type) 207a and another aseptic connection coupling (female type) 207b are combined with each other, membrane strips 2070 which hermetically seal openings of the aseptic connection coupling (male type) 207a and the aseptic connection coupling (female type) 207b, respectively are pulled and peeled off, and the aseptic connection coupling (male type) 207a and the aseptic connection coupling (female type) 207b are locked with each other, whereby the two couplings can be aseptically communicated to each other. As the aseptic connection coupling 207, a commercially available one can be used. For example, the coupling is available from Pall Corporation (USA), Sartorius AG (Germany), Colder Products Company (USA), or the like. The aseptic connection coupling (male type) 207a and the aseptic connection coupling (female type) 207b may be exchanged and used. When the aseptic connection coupling (male type) 207a (or the aseptic connection coupling (female type) 207b) is disposed in the middle of the first flow path 204 and downstream of the liquid delivery port inner lid 103a, the flow path which aseptically connects the inside and outside of the isolator to each other can be shortened. The aseptic connection coupling 207 enables the flow path downstream of the aseptic connection coupling 207 to be freely designed.

In the embodiment, the aseptic sampling apparatus 1 may further include a sample recovering unit which communicates with the first flow path 204, in downstream of the liquid delivery port 103. The sample recovering unit may be means for recovering the sample in the middle of the flow path, and, for example, may be a valve unit 3110 which can recover the sample by switching flow paths, or a rotary autosampler 320 (see FIG. 2) which recovers the sample that is discharged from the flow path, by using a sample recovery tube 321. The valve unit 3110 which can aseptically recover the sample, and which is illustrated in FIG. 1A is preferably used.

Figure 2:
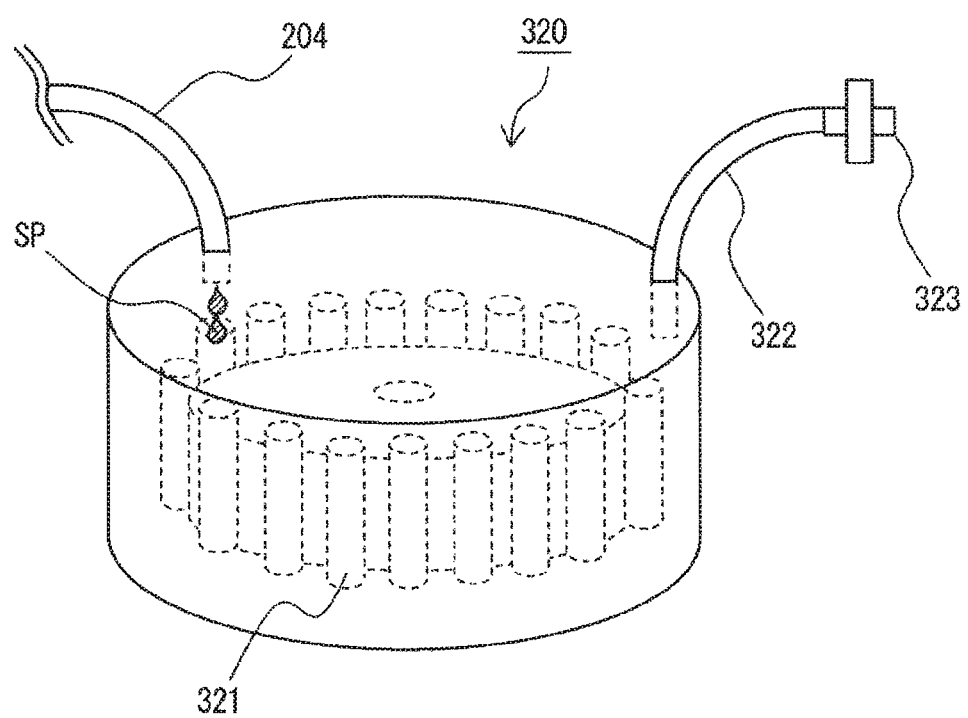
FIG. 2 is a schematic diagram illustrating a part (an autosampler) of the aseptic sampling apparatus of the embodiment of the presently disclosed subject matter.

The valve unit 3110 is exemplarily illustrated in FIG. 1A in a mode in which a typical valve unit is diagrammatically illustrated. The valve unit 3110 may include, in the outer circumference, a first valve flow path 3110a, a second valve flow path 3110b, and a third valve flow path 3110c, and further include a sampling flow path 3110d which is communicated to the first valve flow path 3110a, and the second valve flow path 3110b or the third valve flow path 3110c. In FIG. 1A, a first flow path 204a into which the fluid flows is communicated to the second valve flow path 3110b, the second valve flow path 3110b is communicated to the sampling flow path 3110d, the sampling flow path 3110d is communicated to the first valve flow path 3110a, and the first valve flow path 3110a is communicated to a first flow path 204b from which the fluid is discharged. According to the configuration, the sample SP and the like which flow in from the first flow path 204a are supplied to the sampling flow path 3110d. Moreover, the third valve flow path 3110c is communicated to a flow path of an instrument 311.

When the valve unit 3110 is clockwise rotated while the sampling flow path 3110d is maintained, the first flow path 204a into which the fluid flows is communicated to the first valve flow path 3110a, and the first valve flow path 3110a is communicated to the first flow path 204b from which the fluid is discharged. On the other hand, the sampling flow path 3110d is communicated to the second valve flow path 3110b and the third valve flow path 3110c, and as a result communicated to the flow path of the instrument 311 (see FIG. 1C). According to the configuration, components contained in the sample SP in the sampling flow path 3110d can be measured by the instrument 311.

In the embodiment, the aseptic sampling apparatus 1 may further include, in the isolator 10, a second flow path 206 which communicates with the sampling section 203, a buffer solution supplying section 201 which supplies the fluid to the second flow path 206, and a first pump 208 which is disposed in the second flow path 206. When the first pump 208 is driven, the buffer solution 202 is supplied to the sampling section 203, and the sampling section 203 and the first flow path 204 can be kept clean. In the case where the buffer solution 202 is not supplied through the second flow path 206, the buffer solution 202 may be supplied by, for example, the fluid supplying unit 210. For example, the first pump 208 may be a tube pump (peristaltic pump), or a piezoelectric pump, and any type of pump can be used as far as it can send the fluid. As the buffer solution 202, a solution having characteristics which suppresses a pH variation to a minimum level in order to prevent the properties of materials contained in the sample SP from being changed. For example, useful are a liquid culture medium (such as DMEM or RPM1-1640) which is used for culture of cells, a phosphate buffer solution, a Tris buffer solution, a HEPES buffer solution, a HEPPS buffer solution, a citrate buffer solution, a boric acid buffer solution, or the like. The kind of the buffer solution 202 may be appropriately selected in accordance with the kind and purpose of the sample SP to be recovered. In place of the buffer solution 202, water or a physiological saline solution may be used.

In the embodiment, the first flow path 204 which is downstream of the liquid delivery port 103 (in FIG. 1A, downstream of the valve unit 3110) may include a third flow path 301 and fourth flow path 302 which branch from the first flow path 204.

The third flow path 301 and the fourth flow path 302 may be formed so that the paths again join together into a fifth flow path 303 (FIG. 1A), or that both the third flow path 301 and the fourth flow path 302 are communicated to a waste liquid tank 308 (this configuration is not shown). One of the third flow path 301 and the fourth flow path 302 may include a second pump 307. The third flow path 301 and the fourth flow path 302 are designed so that the valves are opened and closed by a pinch valve switching device 306, and the fluid flows through one of the third and fourth flow paths. When sampling is not performed, as illustrated in FIG. 1A, a first pinch valve 304 is closed, a second pinch valve 305 is simultaneously opened, and the second pump 307 is driven, whereby the buffer solution 202 which is supplied to the sampling section 203 can be flown to the waste liquid tank 308 from the first flow path 204 and through the fourth flow path 302.

Figure 1B:
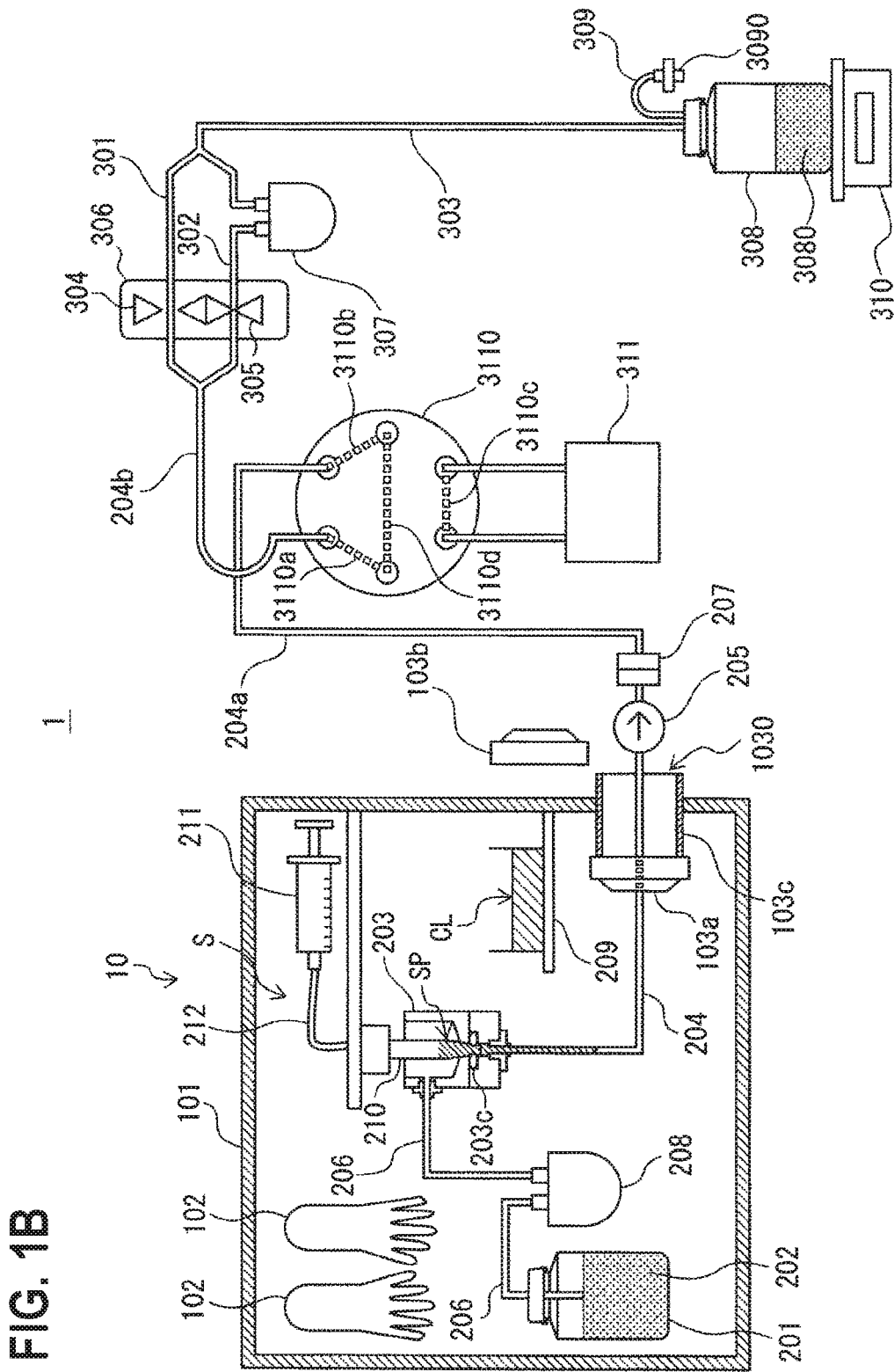

In the case where sampling is to be performed, the buffer solution 202 is discharged from the sampling section 203 and the first flow path 204, the second pinch valve 305 is thereafter closed, the first pinch valve 304 is simultaneously opened, the sample SP which is recovered from cultured cells CL in a cell culturing section 209 is ejected into the discharge flow path 203b of the sampling section 203 by the fluid supplying unit 210, and the compressed gas G is then supplied from the gas supplying unit 211 to the discharge flow path 203b, whereby the sample SP can be delivered from the first flow path 204 to the sampling flow path 3110d of the valve unit 3110 (see FIG. 1B).

Figure 1C:
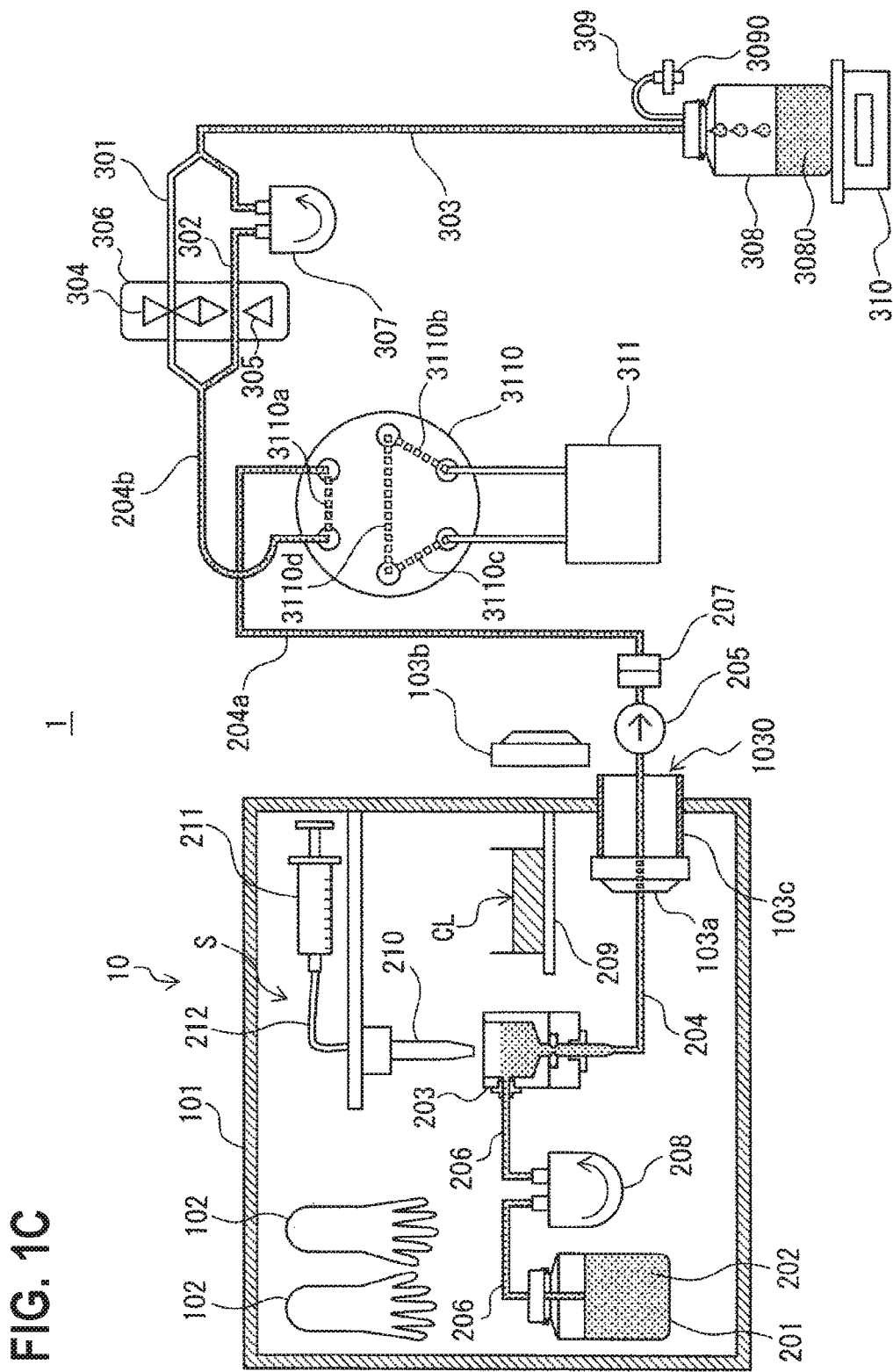

After the sampling, the valve unit 3110 is rotated as illustrated in FIG. 1C, and the flow path is switched over, thereby allowing the sample SP to be inspected by using the instrument 311. At this time, the first pinch valve 304 is again closed, and the second pinch valve 305 is simultaneously opened. Moreover, the first pump 208 is driven, and the second pump 307 is simultaneously driven, thereby causing the sampling section 203, the first flow path 204, and the first valve flow path 3110a of the valve unit 3110 to be washed with an arbitrary amount of the buffer solution 202.

Figure 1D:
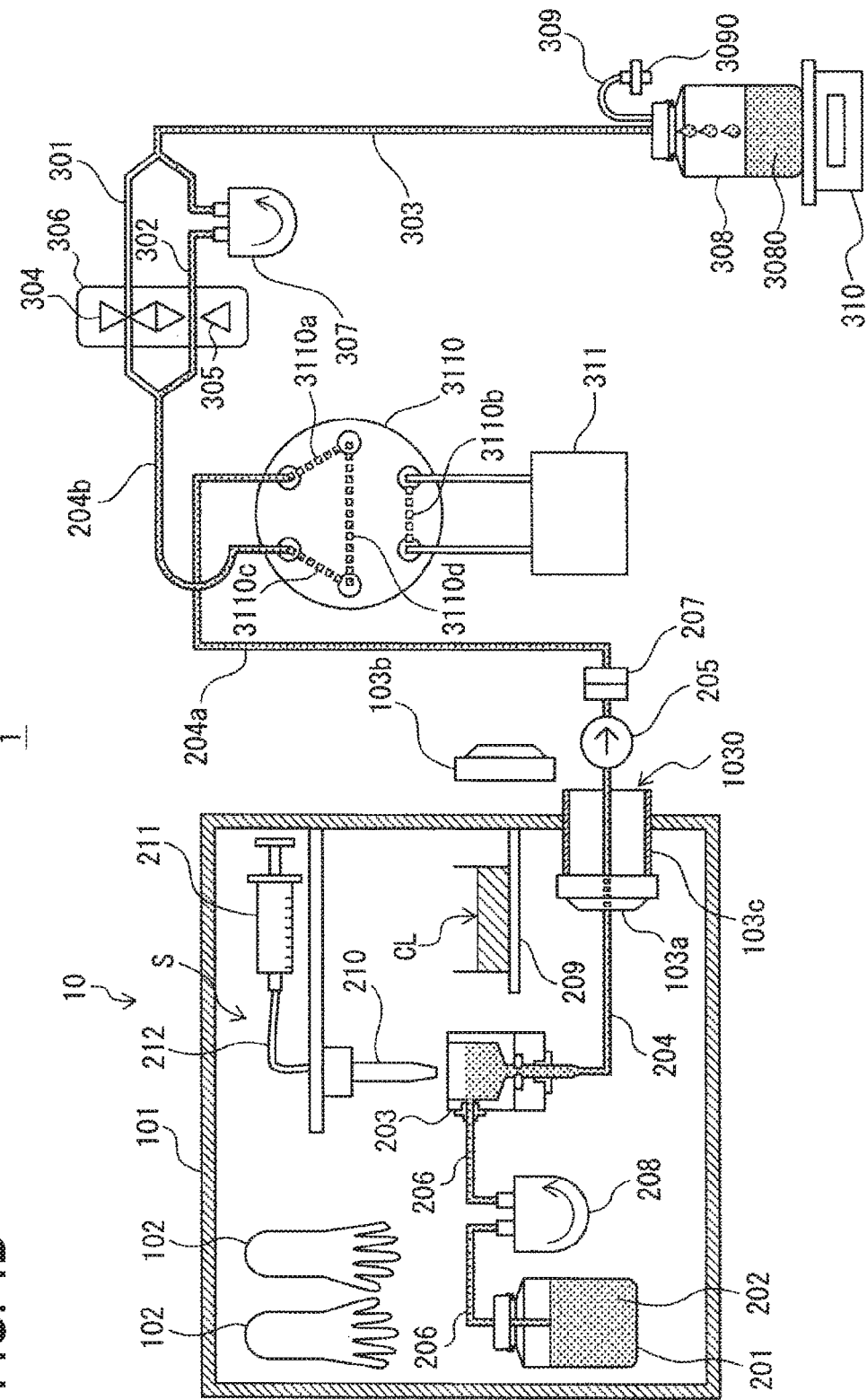

Thereafter, the valve unit 3110 is rotated as illustrated in FIG. 1D, and the flow path is switched over, thereby causing the sampling section 203, the first flow path 204, and the first valve flow path 3110a, sampling flow path 3110d, and third valve flow path 3110c of the valve unit 3110 to be washed with an arbitrary amount of the buffer solution 202 in the same or similar manner as the case of FIG. 1C. After the flow paths are sufficiently washed, preparation for sampling another sample SP is completed. This enables a plurality of samples SP to be recovered without being contaminated.

For example, the second pump 307 may be a tube pump (peristaltic pump), or a piezoelectric pump, and any type of pump can be used as far as it can send the fluid.

FIGS. 3A to 3F are views diagrammatically illustrating the operation of a part of the aseptic sampling apparatus 1 illustrated in FIG. 1A. First, the piston 211a of the gas supplying unit 211 (syringe) is pulled, and the gas G is sucked into the gas supplying unit 211 (see FIG. 3A). As the gas G, the air existing in the isolator 10 may be used. Alternatively, a gas containing 5% CO2 which is suitable for cell culturing may be used, or oxygen may be used. The gas G is requested to be sucked by an amount which is sufficient for allowing the sample SP to be delivered to a target position, and the sucked amount is changed depending on the diameter and length of the first flow path 204. Then, the tip end portion of the fluid supplying unit 210 is immersed in a culture solution for the cultured cells CL, and the piston 211a is pulled to cause an arbitrary amount of the sample SP to be sucked into the fluid supplying unit 210. The fluid supplying unit 210 is moved to a position where the tip end portion is located immediately above the discharge port 203a of the sampling section 203 (the fluid supplying unit 210 (broken lines) in FIG. 1A, see FIG. 3B). Thereafter, a sampling section lifter 203d is raised. The sampling section lifter 203d pushes up the bottom of the sampling section 203, the sampling section 203 is raised, and the tip end portion of the fluid supplying unit 210 is inserted into the discharge flow path 203b (see FIG. 3C). The sampling section lifter 203d is further raised until the seal member 203c disposed in the discharge flow path 203b is in close contact with the tip end portion of the fluid supplying unit 210 (see FIG. 3C).

At the time as the closing of the second pinch valve 305, thereafter, the first pinch valve 304 is opened, and the gas pressure in the first flow path 204 is made equivalent to the atmospheric pressure (see FIG. 1B). When, in this state, the piston 211a is pushed, the sample SP in the fluid supplying unit 210 is discharged from the discharge flow path 203b to the first flow path 204 (see FIG. 3D).

Figure 3E:
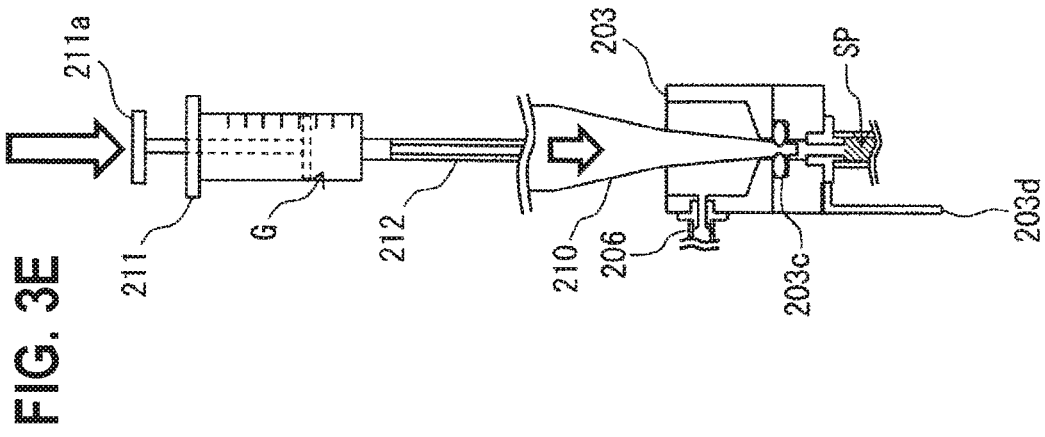

When the piston 211a is further pushed, the gas G is injected into the first flow path 204 (FIG. 3E). Depending on the volume of the injected gas G, the sample SP is flow through the first flow path 204.

Figure 3F:
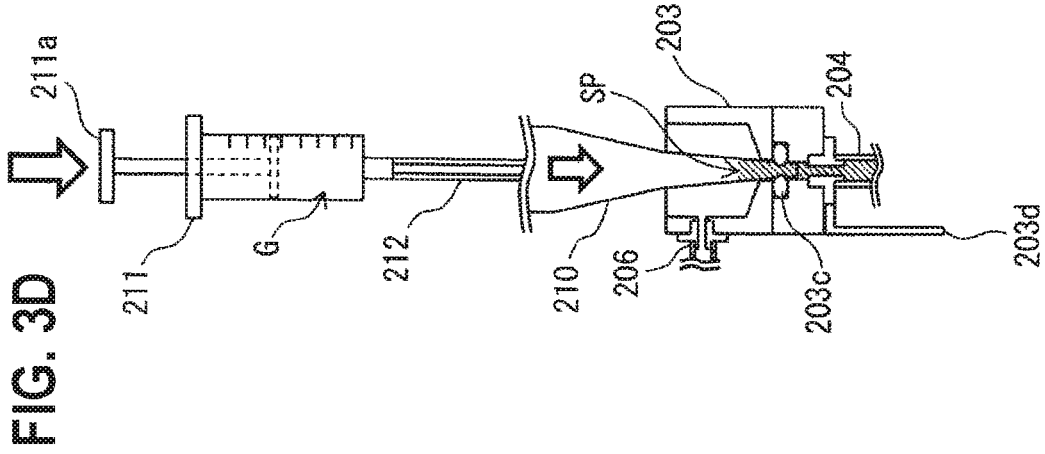

The sample SP is flowed to an arbitrary position, and then the sampling section lifter 203d is lowered. As a result, the sampling section 203 is lowered by its own weight, and the tip end portion of the fluid supplying unit 210 is separated from the sampling section 203, and returned to the original position (FIG. 3F).

Figure 4:
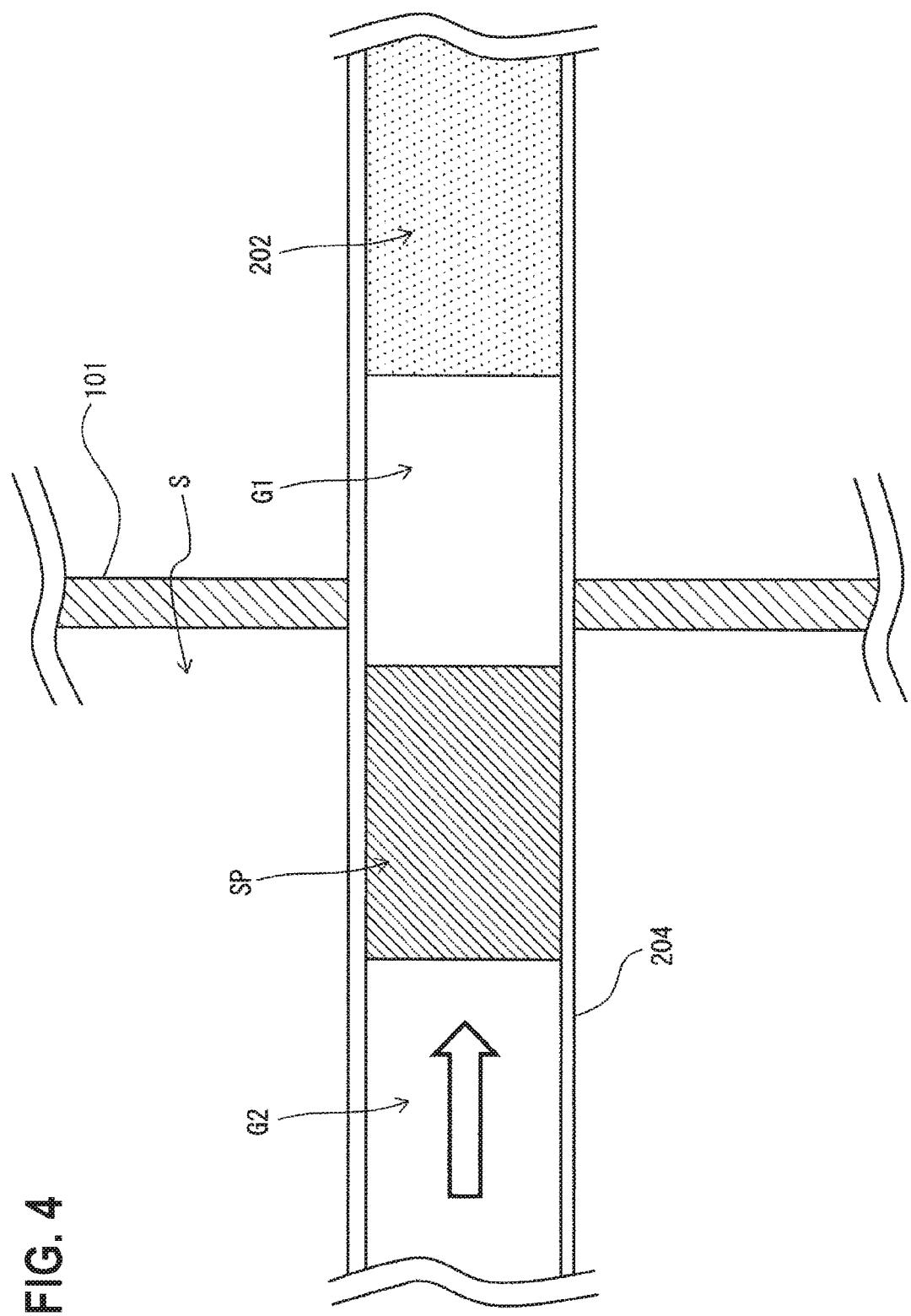
FIG. 4 is a diagram (sectional view) illustrating the state in a flow path of the aseptic sampling apparatus of the embodiment of the presently disclosed subject matter.

FIG. 4 is a view diagrammatically illustrating the manner of the flow of the sample SP in the first flow path 204 of the aseptic sampling apparatus 1 of the presently disclosed subject matter. In the first flow path 204 which is washed by the buffer solution 202, as described above, the disposition of the region where a first gas G1 exists behind a position where the buffer solution 202 exists can prevent the sample SP and the buffer solution 202 from being mixed with each other. The gas G1 may be supplied to the region where the first gas G1 exists, by driving the second pump 307, or by the fluid supplying unit 210.

In the first flow path 204 where the first gas G1 exists, the sample SP is supplied after the first gas G1 by the fluid supplying unit 210 (step (1)). After the sample SP in the first flow path 204, then, a second gas G2 is supplied by the fluid supplying unit 210 to cause the sample SP to be delivered to the outside of the isolator 10 (step (2)). The volume amount of the first gas G1 is not limited as far as it has a value at which the sample SP and the buffer solution 202 are not mixed with each other. The volume amount of the second gas G2 is requested to have a value at which the sample SP can be flowed to the predetermined position of the first flow path 204, and can be changed depending on the diameter and length of the first flow path 204. The first gas G1 and the second gas G2 may be any kinds of gasses, and may be the same kind of gas or different kinds of gases as far as the gases can be used for interposing the sample SP therebetween.

According to the aseptic sampling apparatus 1 of the presently disclosed subject matter, even in the case where the amount of the sample SP is so small (for example, 10 mL, 5 mL, 4 mL, 3 mL, 2 mL, 1 mL, 900 μL, 800 μL, 700 μL, 600 μL, 500 μL, 400 μL, 300 μL, 200 μL, 100 μL, 50 μL, or smaller) that it is difficult for a conventional apparatus to recover the sample while maintaining a sterile environment, the sample SP can be efficiently recovered without contaminating the interior of the isolator 10, and without causing the sample SP to be mixed with the buffer solution 202 or another sample SP. Even in the case where a plurality of samples SP (a plurality of temporal samples of the same specimen, or samples derived from multiple specimens) are handled, the samples can be recovered by using the same flow path, and this contributes to a simplified structure of the apparatus.

<Preparation of Aseptic Sampling Apparatus>

Procedures for setting the aseptic sampling apparatus 1 of the embodiment of the presently disclosed subject matter to a state in which the apparatus can be used will be described (FIGS. 5A to 5D).

Figure 5A:
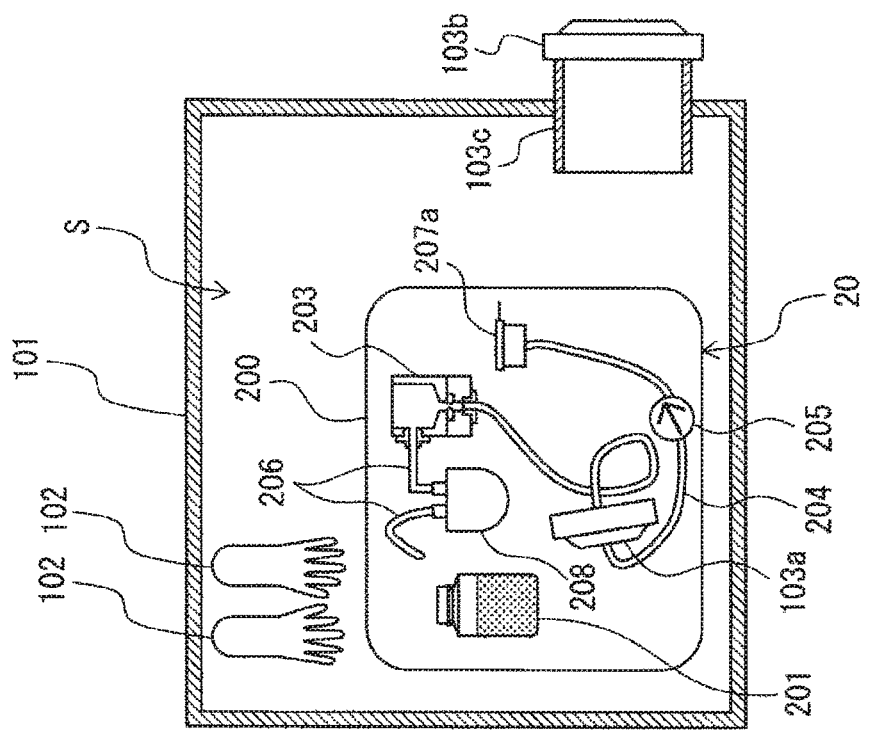
FIGS. 5A to 5D are diagrams illustrating a procedure for installation of the flow path in the aseptic sampling apparatus of the embodiment of the presently disclosed subject matter.

The aseptic sampling apparatus 1 of the presently disclosed subject matter can use an aseptic sampling flow path kit 20. In the embodiment, the aseptic sampling flow path kit 20 may include:

the sampling section 203;

the first flow path 204 which communicates with the sampling section 203; and the at least one one-way valve 205 which is disposed in the first flow path 204, and which limits flow of the fluid in the first flow path 204 to the direction from the sampling section 203 toward the liquid delivery port 103. In another embodiment, as illustrated in FIG. 5A, the aseptic sampling flow path kit 20 may further include: the second flow path 206 which communicates with the sampling section 203; the buffer solution supplying section 201 which supplies the fluid to the second flow path 206; and the first pump 208 which is disposed in the second flow path 206. In further embodiment, the aseptic sampling flow path kit 20 may further include an aseptic connection coupling in the downstream end of the first flow path 204. The above-described members included in the aseptic sampling flow path kit 20 may be enclosed in individual sterilization pouches 200, respectively, or collectively enclosed in the same sterilization pouch 200 as illustrated in FIG. 5A. The members of the aseptic sampling flow path kit 20 which are enclosed in the sterilization pouch 200 are previously sterilized by gamma rays, electron beams, or the like.

Figure 5B:
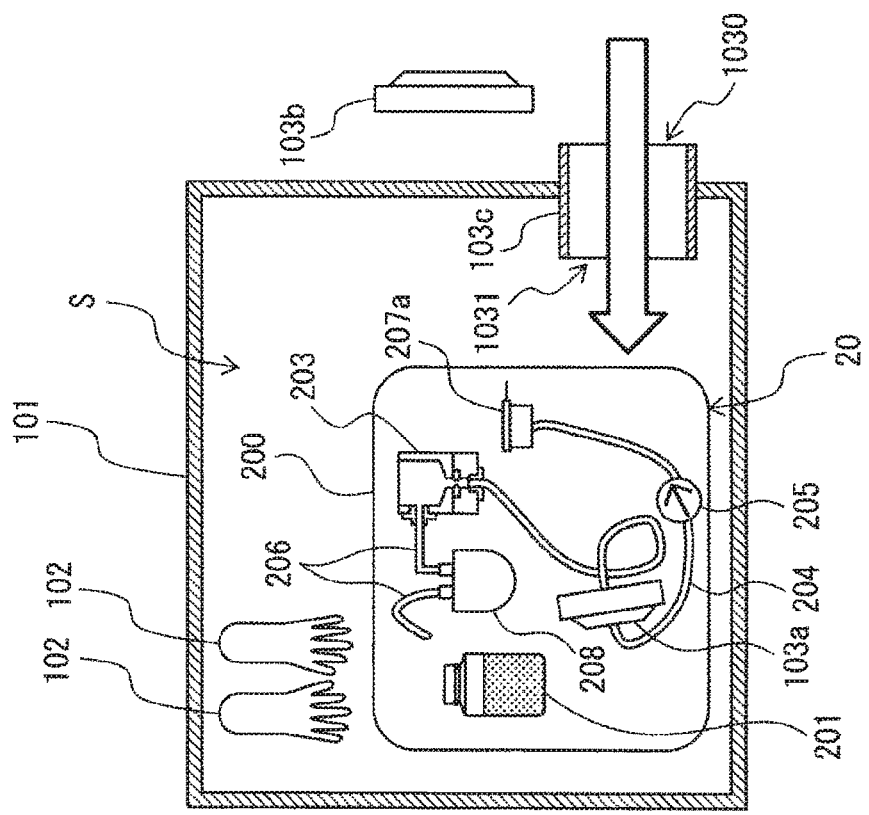

The above-described aseptic sampling flow path kit 20 is carried in into the isolator 10 through the openings of the liquid delivery port body 103c of the isolator, or a decontamination pass box (not shown) which is additionally disposed in the isolator 10 (FIG. 5A). Thereafter, the liquid delivery port opening 1030 which is on the outer side is hermetically closed with the liquid delivery port outer lid 103b, and the interior of the isolator 10 and the aseptic sampling flow path kit 20 are decontaminated (FIG. 5B). The liquid delivery port inner lid 103a may be provided in the state where the lid is enclosed in the sterile bag 200 as illustrated in FIGS. 5A and 5B, or provided into the isolator 10 separately from the sterilization pouch 200.

Figure 5C:
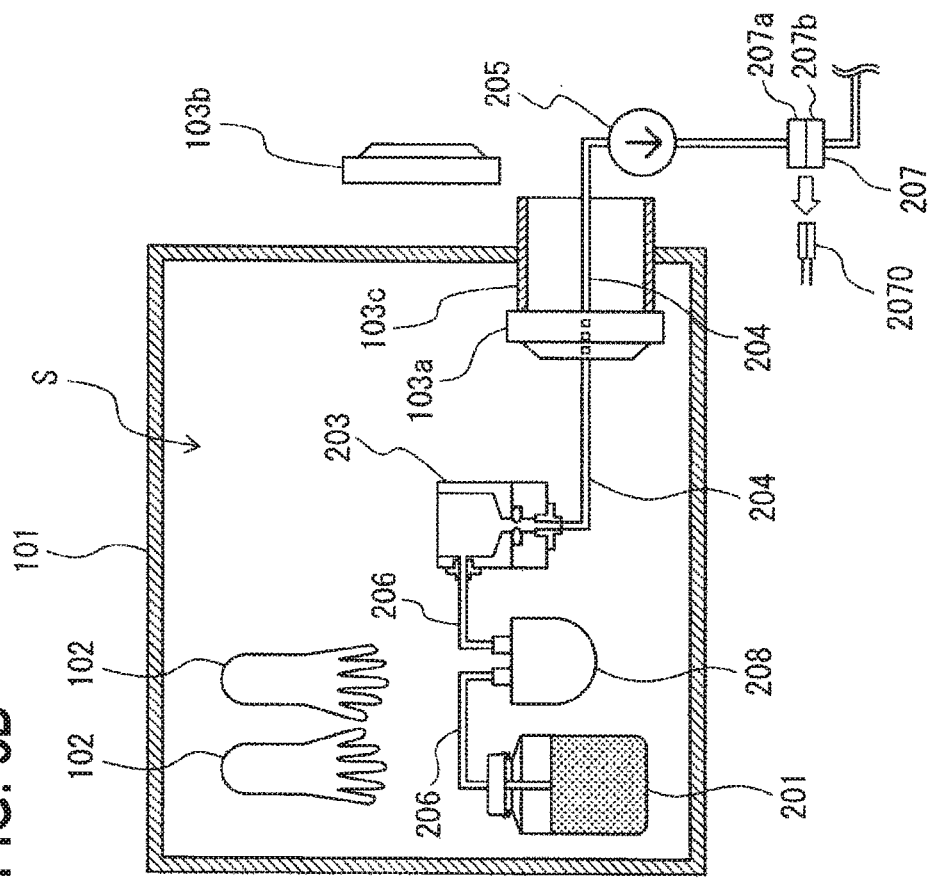
Figure 5D:
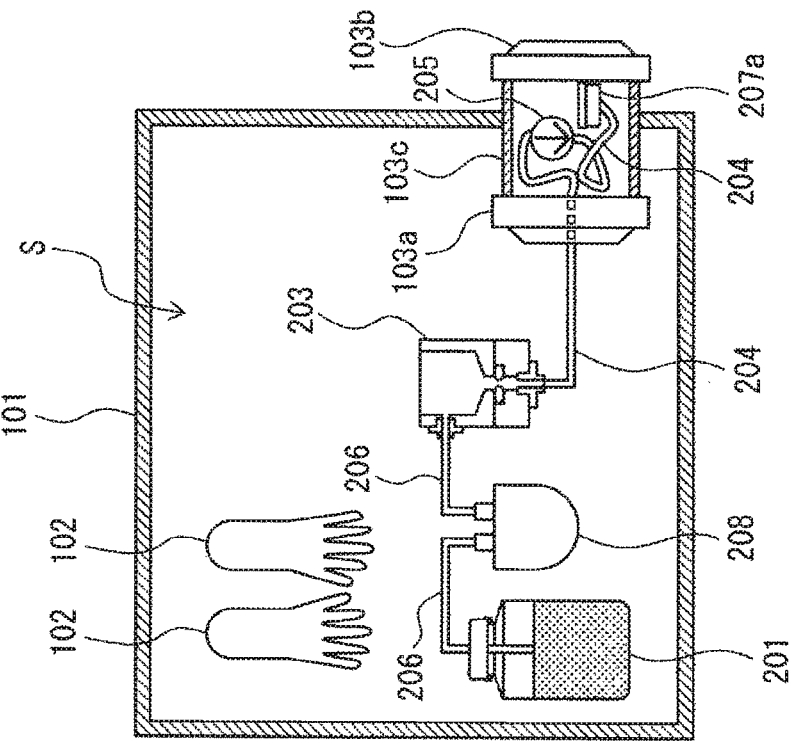

After the decontamination is completed, the sterilization pouch 200 is opened by using gloves 102 which enable the arms of the operator to be inserted from the outside of the isolator 10, and the members are assembled together. The first flow path 204, the one-way valve 205, and the aseptic connection coupling (male type) 207a are placed in the liquid delivery port body 103c, and the liquid delivery port body is hermetically closed with the liquid delivery port inner lid 103a through which the first flow path 204 is passed (FIG. 5C). From the outside of the isolator 10, the liquid delivery port outer lid 103b is detached, and the first flow path 204, the one-way valve 205, and the aseptic connection coupling (male type) 207a are taken out from the liquid delivery port body 103c. Thereafter, the coupling is aseptically communicated to the third flow path 301 which has the aseptic connection coupling (female type) 207b at one end, by using the aseptic connection couplings. As a result, the aseptic sampling apparatus 1 of the presently disclosed subject matter and using the aseptic sampling flow path kit can be used.

Although the presently disclosed subject matter has been described by way of the embodiments, the technical scope of the presently disclosed subject matter is not restricted to the scope of the description of the embodiments. It is obvious to those skilled in the art that various changes or improvements can be made on the embodiments.

What is claimed is:

1. An aseptic sampling apparatus comprising:
    an isolator;
    a liquid delivery port that is disposed in the isolator;
    a sampling section that is disposed inside the isolator, the sampling section including a discharge port and a discharge flow path;
    a first flow path that communicates with the discharge flow path of the sampling section, and that connects an inside and outside of the isolator to each other through the liquid delivery port;
    a fluid supplying unit that supplies a fluid to the sampling section, the fluid supplying unit including a tip end portion configured to be inserted into the discharge port of the sampling unit;
    a gas supplying unit that communicates with the fluid supplying unit and supplies gas to the fluid supplying unit in a state where the tip end portion is inserted into the discharge port;

a seal member that seals a space between the tip end portion inserted into the discharge port and the discharge flow path to prevent the fluid supplied from fluid supplying unit to the discharge flow path from leaking; and an aseptic connection coupling disposed in the first flow path and downstream of the liquid delivery port, wherein the liquid delivery port includes a liquid delivery port body, and a liquid delivery port inner lid to which the liquid delivery port body is fitted, and wherein the first flow path is passed through the liquid delivery port inner lid.

2. The aseptic sampling apparatus according to claim 1, wherein the seal member is disposed in a part of the discharge flow path.

3. The aseptic sampling apparatus according to claim 1, further comprising:

at least one one-way valve which is disposed in the first flow path, and that limits flow of the fluid in the first flow path to a direction from the sampling section toward the liquid delivery port.

4. The aseptic sampling apparatus according to claim 1, further comprising:

a sample recovering unit that communicates with the first flow path in a downstream of the liquid delivery port.

5. The aseptic sampling apparatus according to claim 4, wherein the sample recovering unit is a valve unit.

6. The aseptic sampling apparatus according to claim 1, further comprising:

a second flow path that communicates with the sampling section;

a buffer solution supplying section that supplies the fluid to the second flow path; and a first pump that is disposed in the second flow path.

7. The aseptic sampling apparatus according to claim 1, further comprising:

a third flow path and a fourth flow path that branch from the first flow path in downstream of the liquid delivery port;

a valve switching unit which switches a flow path to one of the third flow path and the fourth flow path; and a second pump that is disposed in the third flow path or the fourth flow path.

8. The aseptic sampling apparatus according to claim 1, wherein the gas supplying unit is a syringe.

9. The aseptic sampling apparatus according to claim 1, wherein the seal member is an O-ring.

10. The aseptic sampling apparatus according to claim 7, wherein the second pump is disposed in only one of the third flow path and the fourth flow path, and wherein the gas supplying unit is configured to move the liquid from the discharge flow path to the first flow path in a state where the other of the third flow path and the fourth flow path is communicated with the flow path by the valve switching unit.

11. A sampling method in the aseptic sampling apparatus according to claim 1, the method comprising:

supplying a sample after a first gas by the fluid supplying unit in the first flow path in which the first gas exists; and supplying a second gas by the fluid supplying unit to deliver the sample to an outside of the isolator, after the sample in the first flow path.

* * * * *